United States Patent
Kugler et al.

(10) Patent No.: US 9,782,561 B2
(45) Date of Patent: Oct. 10, 2017

(54) CATHETER TIP

(71) Applicant: Vascular Solutions, Inc., Minneapolis, MN (US)

(72) Inventors: Chad Kugler, Buffalo, MN (US); John Bridgeman, Minneapolis, MN (US); Derek Stratton, Minneapolis, MN (US); Steve Michael, New Hope, MN (US); Howard Root, Excelsior, MN (US)

(73) Assignee: Vacular Solutions, Inc., Minneapolis, MN (US)

( * ) Notice: Subject to any disclaimer, the term of this patent is extended or adjusted under 35 U.S.C. 154(b) by 249 days.

(21) Appl. No.: 14/860,997

(22) Filed: Sep. 22, 2015

(65) Prior Publication Data
US 2016/0101261 A1 Apr. 14, 2016

Related U.S. Application Data

(60) Provisional application No. 62/061,781, filed on Oct. 9, 2014, provisional application No. 62/203,431, filed on Aug. 11, 2015.

(51) Int. Cl.
*A61M 25/00* (2006.01)
*A61M 5/00* (2006.01)
(Continued)

(52) U.S. Cl.
CPC ...... *A61M 25/005* (2013.01); *A61M 25/0053* (2013.01); *A61M 25/0068* (2013.01)

(58) Field of Classification Search
CPC ........ A61M 2025/006; A61M 25/0043; A61M 25/0045; A61M 25/005; A61M 25/0053; A61M 25/0068
See application file for complete search history.

(56) References Cited

U.S. PATENT DOCUMENTS

| | | | |
|---|---|---|---|
| 3,815,608 A | | 6/1974 | Hodgson et al. |
| 4,898,212 A | * | 2/1990 | Searfoss ............... F16L 11/088 138/124 |

(Continued)

FOREIGN PATENT DOCUMENTS

| | | |
|---|---|---|
| DE | 69424027 | 9/2000 |
| EP | 0661072 A1 | 7/1995 |

(Continued)

OTHER PUBLICATIONS

Notice of Allowance dated Mar. 23, 2017, in U.S. Appl. No. 14/673,966, filed Mar. 31, 2015.

*Primary Examiner* — Quynh-Nhu H Vu
(74) *Attorney, Agent, or Firm* — Gregory W. Smock

(57) ABSTRACT

Catheters and related methods for supporting a guidewire or delivering an agent through a vessel stenosis or other tortuous anatomy are disclosed. A catheter can comprise an elongate shaft body and a polymer tip member disposed at a distal end of the shaft body. The shaft body and the tip member can include a liner, one or both of a braid member or a coil member surrounding the liner, and a polymer cover surrounding the braid member or the coil member. The tip member can further include one or more filaments extending from a position overlapping, underlapping, or abutting a distal end of the braid member or the coil member on their proximal ends to a position distal to the braid member or the coil member on their distal ends. The one or more filaments can include a plurality of filaments arranged in a series of contacting helical windings about the liner, the braid member, or the coil member.

18 Claims, 6 Drawing Sheets

(51) Int. Cl.
*A61M 25/09* (2006.01)
*A61B 5/00* (2006.01)

(56) References Cited

U.S. PATENT DOCUMENTS

| | | | |
|---|---|---|---|
| 5,037,404 A * | 8/1991 | Gold | A61M 25/0053 604/527 |
| 5,057,092 A * | 10/1991 | Webster, Jr. | A61M 25/005 138/123 |
| 5,129,910 A * | 7/1992 | Phan | A61B 17/22031 604/264 |
| 5,183,079 A * | 2/1993 | Blin | F16L 11/086 138/103 |
| 5,263,959 A | 11/1993 | Fischell | |
| 5,423,846 A | 6/1995 | Fischell | |
| 5,454,795 A | 10/1995 | Samson | |
| 5,462,523 A * | 10/1995 | Samson | A61M 25/0043 604/246 |
| 5,554,139 A | 9/1996 | Okajima | |
| 5,569,218 A | 10/1996 | Berg | |
| 5,569,220 A | 10/1996 | Webster | |
| 5,591,142 A * | 1/1997 | Van Erp | A61B 5/6852 604/264 |
| 5,601,537 A | 2/1997 | Frassica | |
| 5,658,264 A | 8/1997 | Samson | |
| 5,662,622 A | 9/1997 | Gore et al. | |
| 5,681,296 A | 10/1997 | Ishida | |
| 5,695,483 A | 12/1997 | Samson | |
| 5,702,373 A | 12/1997 | Samson | |
| 5,769,830 A | 6/1998 | Parker | |
| 5,792,124 A | 8/1998 | Horrigan et al. | |
| 5,853,400 A | 12/1998 | Samson | |
| 5,871,475 A | 2/1999 | Frassica | |
| 5,871,537 A | 2/1999 | Holman et al. | |
| 5,876,385 A | 3/1999 | Ikari et al. | |
| 5,876,386 A | 3/1999 | Samson | |
| 5,885,508 A | 3/1999 | Ishida | |
| 5,891,114 A | 4/1999 | Chien et al. | |
| 5,897,537 A | 4/1999 | Berg et al. | |
| 5,911,715 A | 6/1999 | Berg et al. | |
| 5,927,345 A | 7/1999 | Samson | |
| 5,951,539 A | 9/1999 | Nita et al. | |
| 5,968,064 A | 10/1999 | Selmon et al. | |
| 6,003,561 A | 12/1999 | Brindza et al. | |
| 6,053,903 A | 4/2000 | Samson | |
| 6,059,823 A | 5/2000 | Holman et al. | |
| 6,143,013 A | 11/2000 | Samson et al. | |
| 6,165,163 A | 12/2000 | Chien et al. | |
| 6,217,565 B1 | 4/2001 | Cohen | |
| 6,231,546 B1 | 5/2001 | Milo et al. | |
| 6,235,000 B1 | 5/2001 | Milo et al. | |
| 6,245,098 B1 | 6/2001 | Feeser et al. | |
| 6,319,276 B1 | 11/2001 | Holman et al. | |
| 6,368,316 B1 | 4/2002 | Jansen et al. | |
| 6,485,457 B1 | 11/2002 | Hisamatsu et al. | |
| 6,508,804 B2 | 1/2003 | Sarge et al. | |
| 6,508,806 B1 * | 1/2003 | Hoste | A61M 25/0012 138/124 |
| 6,508,825 B1 | 1/2003 | Selmon et al. | |
| 6,511,458 B2 | 1/2003 | Milo et al. | |
| 6,511,462 B1 | 1/2003 | Itou et al. | |
| 6,533,754 B1 | 3/2003 | Hisamatsu et al. | |
| 6,589,227 B2 | 7/2003 | Sonderskov | |
| 6,638,247 B1 | 10/2003 | Selmon et al. | |
| 6,652,692 B2 | 11/2003 | Pedersen et al. | |
| 6,689,120 B1 | 2/2004 | Gerdts | |
| 6,692,523 B2 | 2/2004 | Holman et al. | |
| 6,719,725 B2 | 4/2004 | Milo et al. | |
| 6,726,712 B1 | 4/2004 | Raeder-Devens et al. | |
| 6,824,553 B1 | 11/2004 | Samson et al. | |
| 6,858,024 B1 | 2/2005 | Berg et al. | |
| 6,926,721 B2 | 8/2005 | Basta | |
| 6,966,891 B2 | 11/2005 | Ookubo et al. | |
| 7,025,758 B2 | 4/2006 | Klint | |
| 7,037,288 B2 | 5/2006 | Rosenberg et al. | |
| 7,104,966 B2 | 9/2006 | Shiber | |
| 7,104,979 B2 | 9/2006 | Jansen et al. | |
| 7,117,703 B2 | 10/2006 | Kato et al. | |
| 7,155,272 B2 | 12/2006 | Yamaguchi et al. | |
| 7,166,100 B2 | 1/2007 | Jordan et al. | |
| 7,291,127 B2 | 11/2007 | Eidenschink | |
| 7,297,302 B2 | 11/2007 | Berg et al. | |
| 7,300,534 B2 | 11/2007 | Wang et al. | |
| 7,322,988 B2 | 1/2008 | Sterud et al. | |
| 7,354,430 B2 | 4/2008 | Pepin | |
| 7,434,437 B2 | 10/2008 | Kato et al. | |
| 7,488,338 B2 | 2/2009 | Eidenschink | |
| 7,491,230 B2 | 2/2009 | Holman et al. | |
| 7,494,478 B2 | 2/2009 | Itou et al. | |
| 7,579,550 B2 | 8/2009 | Dayton et al. | |
| 7,597,830 B2 | 10/2009 | Zhou | |
| 7,615,043 B2 | 11/2009 | Zhou | |
| 7,621,904 B2 | 11/2009 | McFerran et al. | |
| 7,674,411 B2 | 3/2010 | Berg et al. | |
| 7,699,790 B2 | 4/2010 | Simpson | |
| 7,704,245 B2 | 4/2010 | Dittman et al. | |
| 7,740,652 B2 | 6/2010 | Gerdts et al. | |
| 7,758,624 B2 | 7/2010 | Dorn | |
| 7,763,012 B2 | 7/2010 | Petrick et al. | |
| 7,766,896 B2 | 8/2010 | Volk et al. | |
| 7,771,444 B2 | 8/2010 | Patel et al. | |
| 7,785,365 B2 | 8/2010 | Holman et al. | |
| 7,799,068 B2 | 9/2010 | Holman et al. | |
| 7,803,169 B2 | 9/2010 | Shamay | |
| 7,815,599 B2 | 10/2010 | Griffin et al. | |
| 7,824,392 B2 | 11/2010 | Zhou | |
| 7,828,790 B2 | 11/2010 | Griffin | |
| 7,841,994 B2 | 11/2010 | Skujins et al. | |
| 7,854,755 B2 | 12/2010 | Lafontaine et al. | |
| 7,871,430 B2 | 1/2011 | Pavcnik et al. | |
| 7,887,529 B2 | 2/2011 | Eder | |
| 7,896,861 B2 | 3/2011 | McFerran et al. | |
| 7,909,779 B2 | 3/2011 | Shimogami et al. | |
| 7,909,812 B2 | 3/2011 | Jansen et al. | |
| 7,914,515 B2 | 3/2011 | Heideman et al. | |
| 7,914,520 B2 | 3/2011 | Kennedy, II | |
| 7,927,784 B2 | 4/2011 | Simpson | |
| 7,955,313 B2 | 6/2011 | Boismier | |
| 7,968,038 B2 | 6/2011 | Dittman et al. | |
| 7,981,091 B2 * | 7/2011 | Root | A61M 25/0068 604/264 |
| 7,985,213 B2 | 7/2011 | Parker | |
| 7,985,214 B2 | 7/2011 | Garabedian et al. | |
| 7,998,132 B2 | 8/2011 | Gregorich et al. | |
| 8,021,352 B2 | 9/2011 | Slazas et al. | |
| 8,092,509 B2 | 1/2012 | Dorn et al. | |
| 8,109,872 B2 | 2/2012 | Kennedy, II et al. | |
| 8,109,985 B2 | 2/2012 | Meyer et al. | |
| 8,118,804 B2 | 2/2012 | Takagi et al. | |
| 8,124,876 B2 | 2/2012 | Dayton et al. | |
| 8,172,863 B2 | 5/2012 | Robinson et al. | |
| 8,202,246 B2 | 6/2012 | Kugler et al. | |
| 8,206,373 B2 | 6/2012 | Zhou | |
| 8,221,387 B2 | 7/2012 | Shelso et al. | |
| 8,226,702 B2 | 7/2012 | Raeder-Devens et al. | |
| 8,231,647 B2 | 7/2012 | Eidenschink | |
| 8,235,942 B2 | 8/2012 | Frassica et al. | |
| 8,251,976 B2 | 8/2012 | Zhou | |
| 8,257,314 B2 | 9/2012 | Agnew | |
| 8,303,570 B2 | 11/2012 | Gregorich et al. | |
| 8,317,772 B2 * | 11/2012 | Jansen | A61M 25/005 604/523 |
| 8,328,791 B2 | 12/2012 | Griffin | |
| 8,337,425 B2 | 12/2012 | Olson et al. | |
| 8,366,674 B2 | 2/2013 | Frassica et al. | |
| 8,372,056 B2 | 2/2013 | Eder | |
| 8,377,035 B2 | 2/2013 | Zhou et al. | |
| 8,382,739 B2 | 2/2013 | Walak | |
| 8,387,347 B2 | 3/2013 | Imai et al. | |
| 8,403,912 B2 | 3/2013 | McFerran et al. | |
| 8,414,477 B2 | 4/2013 | Tallarida et al. | |
| 8,419,658 B2 | 4/2013 | Eskuri | |
| 8,454,578 B2 | 6/2013 | Leeflang et al. | |
| 8,486,010 B2 | 7/2013 | Nomura | |

(56) References Cited

U.S. PATENT DOCUMENTS

| | | | |
|---|---|---|---|
| 8,496,679 B2 | 7/2013 | Robinson et al. | |
| 8,500,785 B2 | 8/2013 | Gunderson | |
| 8,523,841 B2 | 9/2013 | Itou et al. | |
| 8,535,369 B2 | 9/2013 | Raeder-Devens et al. | |
| 8,540,695 B2 * | 9/2013 | Shimogami | A61M 25/005 604/525 |
| D690,806 S | 10/2013 | Nakayama et al. | |
| 8,551,073 B2 | 10/2013 | Katoh et al. | |
| 8,556,914 B2 | 10/2013 | Vrba | |
| 8,574,219 B2 | 11/2013 | Adams et al. | |
| 8,603,066 B2 | 12/2013 | Heidman et al. | |
| 8,764,631 B2 | 7/2014 | Frassica | |
| 8,870,755 B2 * | 10/2014 | Frassica | A61B 1/00082 600/115 |
| 8,955,552 B2 * | 2/2015 | Nanney | F16L 11/087 138/124 |
| 9,636,477 B2 | 5/2017 | Root et al. | |
| 2003/0191451 A1 | 10/2003 | Gilmartin | |
| 2004/0002677 A1 | 1/2004 | Gentsler | |
| 2004/0087885 A1 * | 5/2004 | Kawano | A61M 25/0012 604/8 |
| 2005/0021002 A1 | 1/2005 | Deckman et al. | |
| 2005/0171478 A1 | 8/2005 | Selmon et al. | |
| 2005/0222585 A1 | 10/2005 | Miyata et al. | |
| 2006/0100602 A1 | 5/2006 | Klint | |
| 2006/0151043 A1 | 7/2006 | Nanney et al. | |
| 2006/0258987 A1 | 11/2006 | Lentz et al. | |
| 2006/0264904 A1 | 11/2006 | Kerby et al. | |
| 2007/0060996 A1 * | 3/2007 | Goodin | A61F 2/95 623/1.11 |
| 2008/0039823 A1 | 2/2008 | Shimogami et al. | |
| 2008/0108974 A1 | 5/2008 | Roth | |
| 2008/0185063 A1 * | 8/2008 | Bieszczad | F16L 11/085 138/126 |
| 2009/0048657 A1 | 2/2009 | Duran et al. | |
| 2009/0112063 A1 | 4/2009 | Bakos et al. | |
| 2009/0124899 A1 | 5/2009 | Jacobs et al. | |
| 2009/0312831 A1 | 12/2009 | Dorn | |
| 2010/0256727 A1 | 10/2010 | Gerdts et al. | |
| 2010/0297334 A1 | 11/2010 | Weber | |
| 2011/0009889 A1 | 1/2011 | Shamay | |
| 2011/0035927 A1 | 2/2011 | Griffin et al. | |
| 2011/0257042 A1 | 10/2011 | Simpson | |
| 2011/0297307 A1 | 12/2011 | Slazas et al. | |
| 2012/0016344 A1 | 1/2012 | Kusakabe | |
| 2012/0116491 A1 | 5/2012 | Meyer et al. | |
| 2012/0136340 A1 | 5/2012 | Tanioka | |
| 2012/0271174 A1 | 10/2012 | Iwahashi | |
| 2012/0323251 A1 | 12/2012 | Kugler et al. | |
| 2013/0023858 A1 | 1/2013 | Dayton et al. | |
| 2013/0072905 A1 | 3/2013 | Jansen et al. | |
| 2013/0096535 A1 | 4/2013 | Gregorich et al. | |
| 2013/0110144 A1 | 5/2013 | Olson et al. | |
| 2013/0116721 A1 | 5/2013 | Takagi et al. | |
| 2013/0137977 A1 | 5/2013 | Eder | |
| 2013/0296907 A1 | 11/2013 | Robinson et al. | |
| 2013/0331820 A1 | 12/2013 | Itou et al. | |
| 2015/0051541 A1 * | 2/2015 | Kanemasa | A61M 25/0009 604/95.04 |
| 2016/0101262 A1 | 4/2016 | Root et al. | |
| 2017/0156750 A1 | 6/2017 | Root et al. | |

FOREIGN PATENT DOCUMENTS

| | | |
|---|---|---|
| EP | 1096965 B1 | 12/2007 |
| JP | 07323090 A | 12/1995 |
| JP | 3659664 B2 | 6/2005 |
| JP | 2007029120 A | 2/2007 |
| JP | 2007061311 A | 3/2007 |
| JP | 2014097090 A1 | 5/2014 |
| KR | 101314714 B1 | 10/2013 |
| WO | 2005105192 A1 | 11/2005 |

* cited by examiner

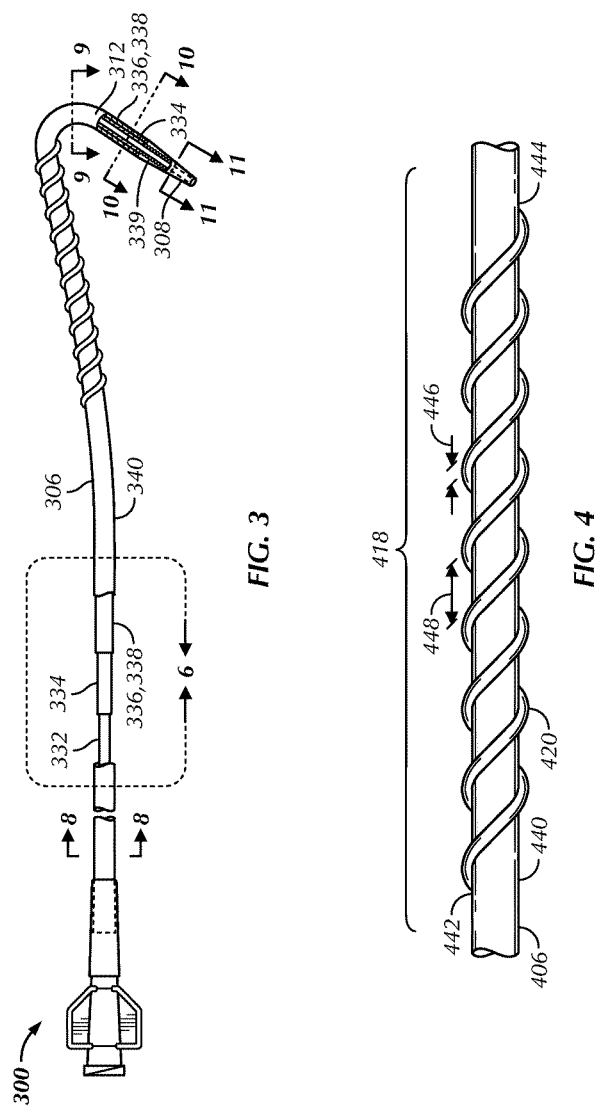

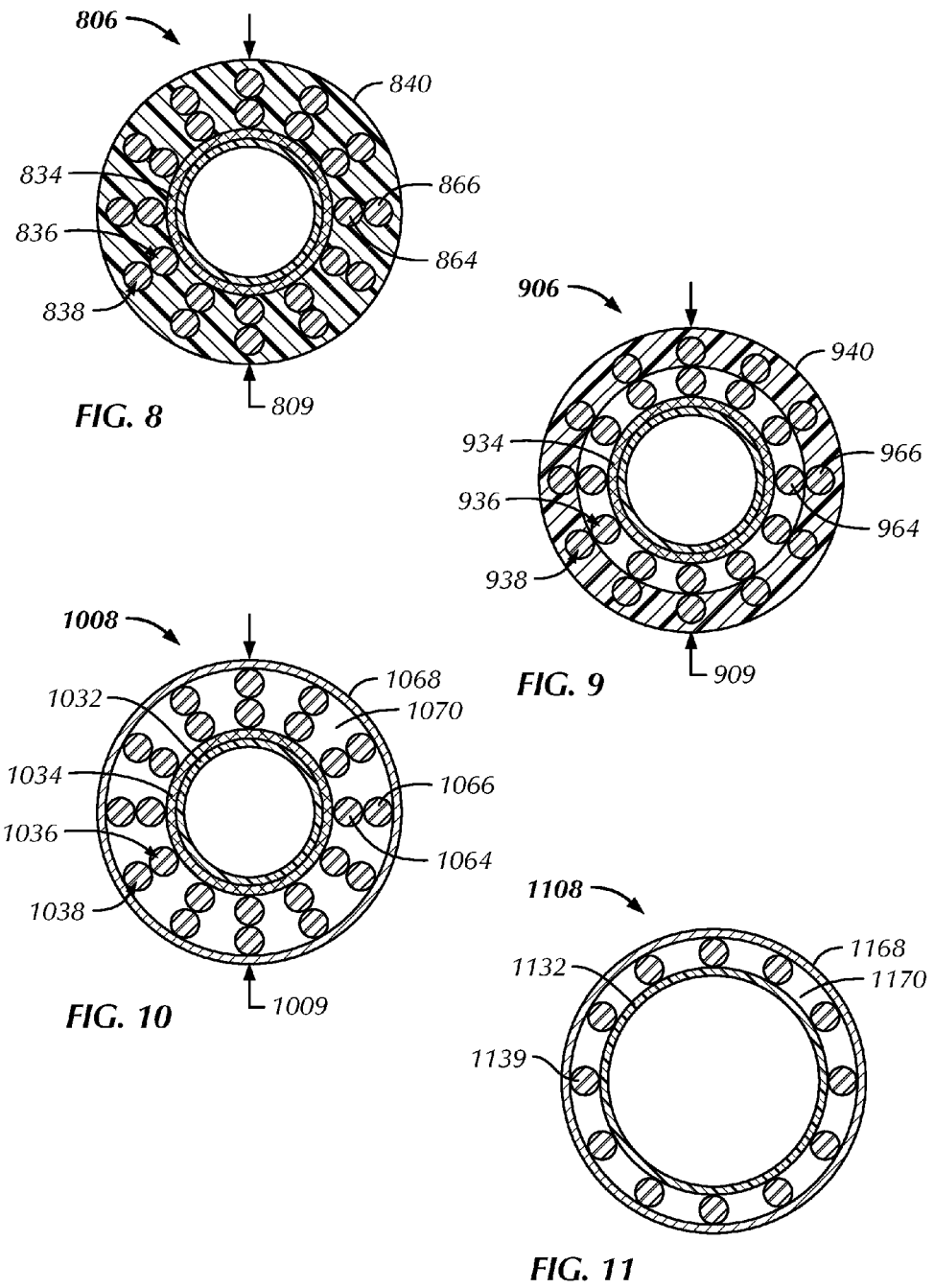

CATHETER TIP

CLAIM OF PRIORITY

This non-provisional patent document claims the benefit of priority under 35 U.S.C. §119(e) to U.S. Provisional Patent Application Ser. No. 62/061,781, entitled "CATHETER" and filed on Oct. 9, 2014, and U.S. Provisional Patent Application Ser. No. 62/203,431, entitled "CATHETER TIP" and filed on Aug. 11, 2015, each of which is herein incorporated by reference in its entirety.

TECHNICAL FIELD

The subject matter of this patent document relates to the field of medical devices. More particularly, but not by way of limitation, the subject matter relates to catheters and related methods for supporting a guidewire or delivering a radiopaque, diagnostic or therapeutic agent.

BACKGROUND

A variety of catheters exist for percutaneous insertion into a subject's vascular system to accomplish diagnostic or therapeutic objectives using the Seldinger technique. As part of the Seldinger technique, a guidewire can be inserted through the lumen of a hollow needle and made to enter the vascular system. A catheter can fit over and slide along the guidewire as it passes through vasculature. The guidewire alone or with the help of the catheter can be incrementally maneuvered through the vasculature to a target (diseased) site.

Catheters are typically introduced through a large artery, such as those found in the groin or neck, and then passed through ever-narrower regions of the vascular system until reaching the target site. Often, such pathways will wind back upon themselves in a multi-looped path. The quest to provide treatment options for narrowing and winding vessels and other lumens has given rise to the need to reduce catheter diametrical size, yet retain a catheter's favorable structural properties.

OVERVIEW

Various structural properties can be used to describe catheters. "Pushability," for example, can be used to describe a catheter's axial strength to facilitate movement of its distal end through vascular passages or other body lumens by applying an axial pushing force near its proximal end. A related characteristic, "torqueability," can be used to describe the ability to rotate the catheter's distal end by rotating its proximal end. "Flexibility," particularly along a distal portion of the catheter, becomes increasingly important as the catheter enters winding or tortuous passages. Another characteristic that becomes more important with increased curvature of passages is the ability to resist kinking.

The present inventors recognize a difficulty in placing existing "push-to-advance" catheter designs, which include a relatively stiff, thick wall to navigate a vascular passage. The present inventors further recognize that as higher demands for length have been placed on catheters, a competing difficulty of smaller catheter diametrical size, particularly along catheter distal end portions, has developed.

The present catheters overcome drawbacks of existing catheter designs by providing a structure that, despite a reduction in distal diameter, maintains favorable structural properties and advanceability along its length. A catheter can comprise an elongate shaft body and a tip member disposed at a distal end of the shaft body. The shaft body can extend from a proximal end to the distal end and can define an inner lumen. The shaft body and the tip member can include a liner, one or both of a braid member or a coil member surrounding the liner, and a polymer cover surrounding the braid member or the coil member. The tip member can further include one or more filaments extending from a position overlapping, underlapping, or abutting a distal end portion of the braid member or the coil member on their proximal ends to a position distal to the braid member or the coil member on their distal ends. The one or more filaments can include a plurality of filaments optionally arranged in a series of contacting helically windings about the liner, the braid member, or the coil member. Clinical bench testing has demonstrated that the catheters exhibit pushability, flexibility, an ability to transfer torque in a controllable manner without kinking or failure, and an ability to be propelled along a blood vessel.

The present methods can include advancing a distal end of a guidewire to a location proximate a stenosis or other narrowing in a blood vessel; guiding a catheter over the guidewire; using the guidewire as a rail, advancing a distal end of the catheter to the location proximate the stenosis or narrowing; rotating the catheter in a first direction and advancing it into the stenosis or narrowing; and advancing the guidewire through the stenosis or narrowing with the support of the catheter. The guidewire can be inserted into an inner lumen of the catheter, where the inner lumen is defined, in part, by a liner, a braid member, a coil member, one or more filaments, and a polymer cover. Rotation of the catheter in the first direction can engage one or more helical threads on an outer surface of the polymer cover with the stenosis or wall of the blood vessel, which can help advance the catheter into and progressively through the stenosis or narrowing.

These and other examples and features of the present catheters and related methods will be set forth, at least in part, in the following Detailed Description. This Overview is intended to provide non-limiting examples of the present subject matter—it is not intended to provide an exclusive or exhaustive explanation. The Detailed Description below is included to provide further information about the present catheters and related methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

FIG. 3 illustrates staggered cutaways of a catheter, as constructed in accordance with at least one embodiment.

FIG. 4 illustrates an enlarged side view of a distal end portion of a catheter's shaft body, as constructed in accordance with at least one embodiment.

FIG. 8 illustrates a cross-section of a proximal end portion of a catheter's shaft body, such as a cross-section along line 8-8 of FIG. 3.

FIG. 9 illustrates a cross-section of a distal end portion of a catheter's shaft body, such as a cross-section along line 9-9 of FIG. 3.

FIG. 10 illustrates a cross-section of a proximal end portion of a catheter's polymer tip member, such as a cross-section along line 10-10 of FIG. 3.

FIG. 11 illustrates a cross-section of a distal end portion of a catheter's polymer tip member, such as a cross-section along line 11-11 of FIG. 3.

Figure 1:
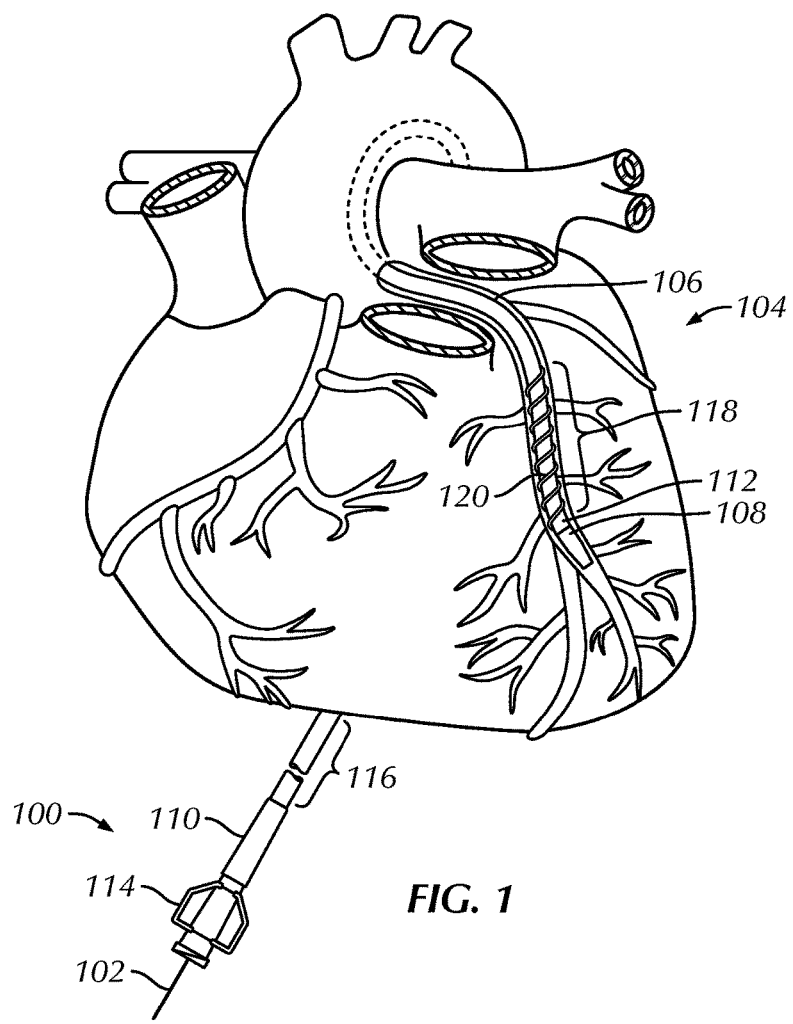
FIG. 1 illustrates a schematic view of a catheter, as constructed in accordance with at least one embodiment, located in coronary vasculature.

The drawing figures are not necessarily to scale. Certain features and components may be shown exaggerated in scale or in schematic form and some details may not be shown in the interest of clarity and conciseness.

DETAILED DESCRIPTION

FIG. 1 illustrates a catheter 100 for supporting a guidewire 102 or delivering a radiopaque, diagnostic or therapeutic agent through a vessel stenosis or other tortuous anatomy of coronary vasculature 104, as constructed in accordance with at least one embodiment. The catheter 100 can be used in peripheral and coronary applications, but its primary benefit is believed to be in coronary applications where the vessels, relative to peripheral vessels, are smaller, more tortuous and more difficult to reach.

The catheter 100 can include a shaft body 106 and a polymer tip member 108 and can be delivered through a surgically created opening in a femoral or radial artery, for example. The shaft body 106 can extend from a proximal end 110 to a distal end 112 and can define an inner lumen. The tip member 108 can be connected to the distal end 112 of the shaft body 106 and can include a lumen coaxial with the shaft body's inner lumen to facilitate receipt or delivery of the guidewire or agent. A luer hub 114 can be connected to the proximal end 110 of the shaft body 106 to facilitate connection to other medical devices, such as valves, syringes or adaptors, and to provide access to the shaft body's inner lumen.

A proximal portion 116 of the shaft body 106 can be designed to be less flexible than its distal portion 118. The less flexible proximal portion 116 can provide enhanced axial and circumferential strength to the catheter 100 for greater pushability. The distal portion 118 can provide the catheter 100 with enhanced flexibility for negotiating winding or tortuous vascular passages. An outer surface portion of the shaft body 106, such as the distal end portion 118, can optionally include one or more helical threads 120 to enhance catheter delivery or withdrawal through rotational movements.

Figure 2:
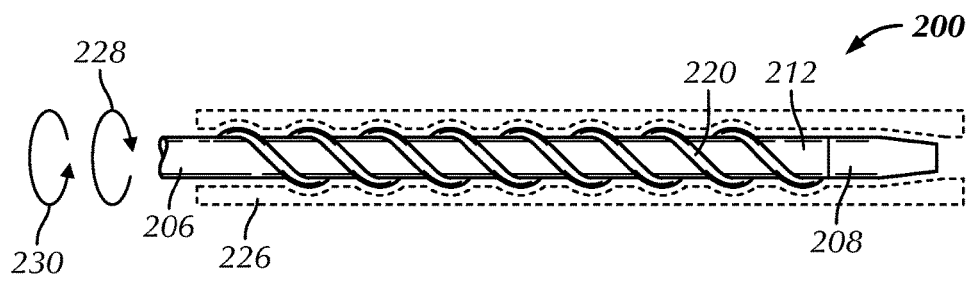
FIG. 2 illustrates a distal end portion of a catheter, as constructed in accordance with at least one embodiment, with one or more helical threads located on an outer surface of a shaft body being engaged with a vessel wall.

FIG. 2 illustrates engagement between a vessel wall 226 and one or more helical threads 220 projecting from an outer surface portion of a catheter's shaft body 206 and terminating before a polymer tip member 208. Optionally, the helical threads 220 can extend along an outer surface portion of the catheter's shaft and along an outer surface of the tip member 208 (e.g., to the distal end of the tip member) and/or be configured such that the one or more helical threads include a depression (rather than projection) of the outer surface of the shaft body 206 or tip member 208. A treating clinician can gently urge the catheter 200 through vasculature far enough to engage the helical threads 220 with the vessel wall 226. The clinician can then rotate a proximal end of the catheter 200 in the direction 228 of the helical threads, such as in a clockwise direction, to advance the catheter through small and tortuous vessels to a target site. The helical threads 220 can have a sufficient radial height, relative to the outer surface of the shaft body 206, to provide a longitudinal pull on the vessel wall 226 or a stenosis, if present, when rotated. The catheter 200 can be removed by rotating the proximal end of the catheter in a direction 230 opposite the direction of delivery, such as in a counterclockwise direction.

A side view of a catheter 300 including its shaft body 306 and polymer tip member 308 is illustrated in FIG. 3. The shaft body 306 can include multiple components, including an inner liner 332, a reinforcing braid member 334, a coil member having one or more coil layers 336, 338 wound in opposing directions, and an outer polymer cover 340. The tip member 308 can include a non-tapered proximal portion and a tapered distal portion (both of which are shown partially cutaway). The proximal portion of the tip member 308 can receive distal ends of the braid member 334 and coil layers 336, 338. The proximal and distal portions of the tip member 308 can include one or more filaments 339 that extend from a position overlapping, underlapping, or abutting a distal end portion of the braid member 334 or the coil layers 336, 338 on their proximal ends to a position distal to the braid member 334 and the coil layers 336, 338 on their distal ends.

The sandwiching of the braid member 334 and coil layers 336, 338 between the inner liner 332 and the outer polymer cover 340 combined with the polymer tip member's 308 receipt of distal ends of the braid member 334 and coil layers 336, 338 and inclusion of one or more filaments 339, which can extend distal to the braid member 334 and the coil layers 336, 338, permit the catheter 300 to be formed at a reduced thickness while maintaining a favorable balance of structural characteristics along its length.

FIG. 4 illustrates one or more helical threads 420 on an outer surface portion of a polymer cover 440, which can help propel a catheter through a blood vessel when rotated. The helical threads 420 can be positioned around a distal end portion 418 of a shaft body 406 and project radially outward. Ends 442, 444 of the helical threads 420 can be tapered from zero to full height in one-half turn of the helix, for example, to facilitate gentle, gradual displacement of a vessel wall or stenosis by the threads when the catheter is rotated for advancement and retraction. Thread width 446 and thread pitch 448 can be designed so that the vessel wall or stenosis does not bridge between adjacent turns of the threads 420 but rather is only displaced in a manner closely conforming to the threads 420, thereby providing the necessary longitudinal grip on the vessel wall or stenosis for advancing and retracting the catheter.

In various examples, the one or more helical threads 420 include a polymer member wound around the polymer cover 440. The polymer member can be a strip of a synthetic fiber (e.g., nylon or polyester) having a fully-round cross-sectional shape of about 0.05 mm-0.2 mm in diameter prior to being bonded to the polymer cover 440. The polymer member can have a melting temperature higher than a melting temperature of the polymer cover 440 so that the helical threads 420 can be thermally bonded to, and inlaid in, the polymer cover 440. Alternatively, the helical threads 420 can be attached to the polymer cover 440 by sonic or adhesive bonding. The polymer member can, for example, extend 20-50 turns around the outer surface of the polymer cover 440 at a uniform pitch of 1.0 mm-2.0 mm, resulting in a threaded section 2-8 cm in length. Optionally, the polymer member can be reinforced with wire or filament fibers.

Figure 5:
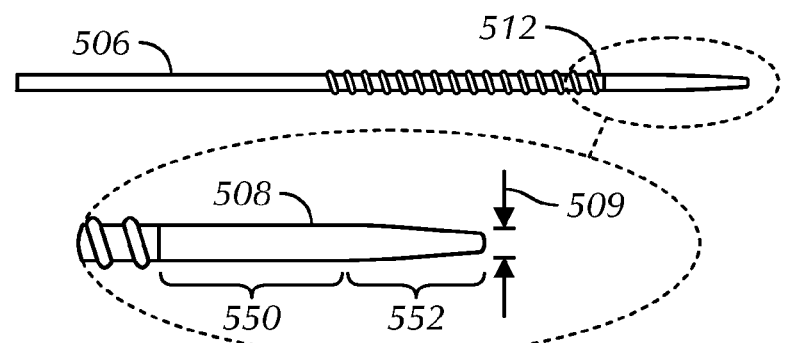
FIG. 5 illustrates a catheter's polymer tip member, including a non-tapered proximal portion and a tapered distal portion, coupled with a distal end of the catheter's shaft body, as constructed in accordance with at least one embodiment.

FIG. 5 illustrates a polymer tip member 508 that can be coupled with a distal end 512 of a catheter's shaft body 506. The polymer tip member 508 can facilitate tracking through tortuous vasculature using its inherent flexibility and low profile configuration including a distal diameter 509 in a range of 0.3 mm to 0.6 mm. In varying examples, the polymer tip member 508 includes a covering material having a durometer softer than a covering material of the shaft body 506. The softer polymer tip member 508 cooperates with the harder durometer shaft body 506 by readily bending in tortuous vessels when pushed therethrough. The polymer tip member 508 can be impregnated with a radiopaque filler material, such as barium sulfate, bismuth trioxide, bismuth carbonate, powdered tungsten, powdered tantalum or the like, so that its location within a subject's body can be radiographically visualized.

In the example of FIG. 5, the polymer tip member 508 includes a non-tapered proximal portion 550 and a tapered distal portion 552. The proximal portion 550 and the distal portion 552 can have a similar length, or the proximal portion 550 can be longer than the distal portion 552. In an example, the polymer tip member 508 has a length of 11 mm, including a 6 mm proximal portion 550 and a 5 mm distal portion 552.

Figure 6:
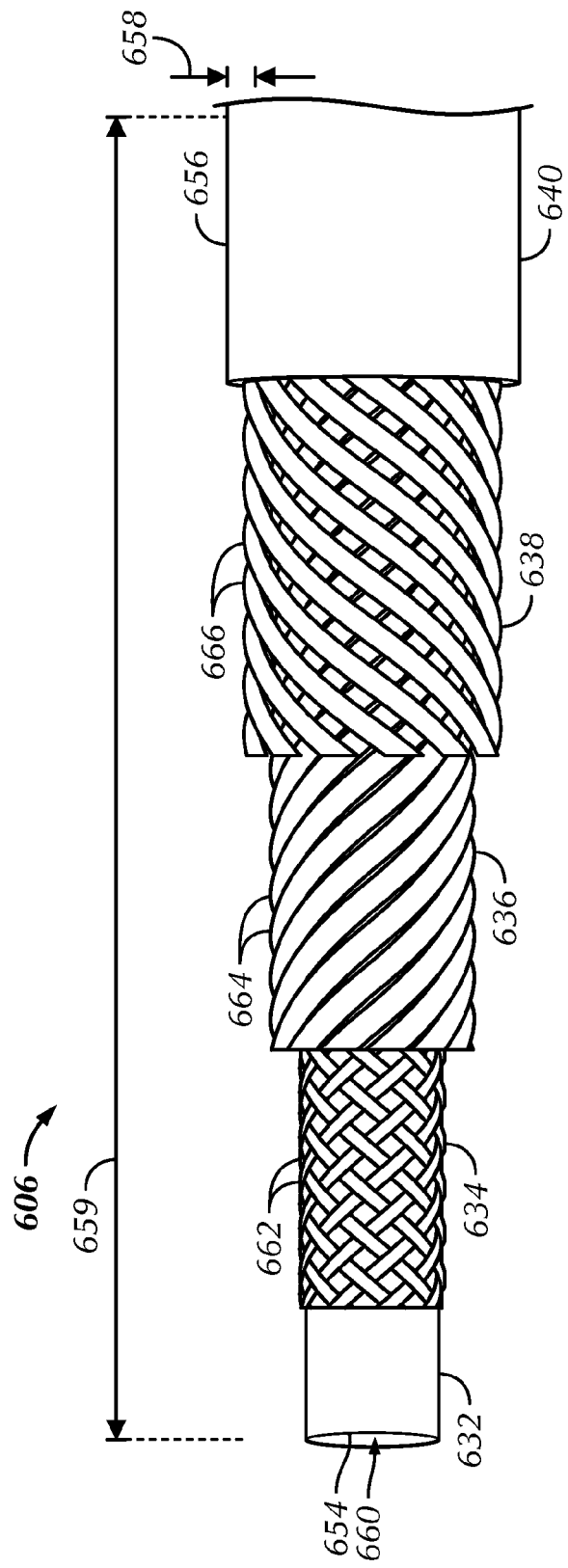
FIG. 6 illustrates staggered cutaways of a catheter's shaft body, as constructed in accordance with at least one embodiment.

FIG. 6 illustrates the multiple components of a catheter's shaft body 606, as constructed in accordance with at least one embodiment. The multiple components can include a liner 632, a braid member 634, a coil member having multiple coil layers 636, 638, and a polymer cover 640. The shaft body 606 can define an inner lumen 660 and can have an inner surface 654, an outer surface 656, a wall thickness 658 in a radial direction, and a length 659 of 60 cm-200 cm, for example.

The liner 632 can extend the length of the shaft body 606 and into and through the catheter's tip member. The liner 632 can be formed of a material providing high lubricity (e.g., polytetrafluoroethylene (PTFE) or polyethylene) to reduce the forces required to advance a guidewire or other member through the catheter.

Surrounding the liner 632 can be a braid member 634 formed of multiple elongate strands 662 helically-wound in opposite directions and interbraided with one another to form multiple crossings. The braid member 634 can extend the length of the shaft body 606 and partially into the catheter's tip member to enhance the torqueability of the catheter and minimize its kinking when flexed. The strands 662 can be formed of stainless steel or another high tensile strength material and can be axially spaced apart to define multiple pics. The axial length of the pics, as determined by the strand spacing, can be selected to influence one or more of the catheter's pushability, torqueability, flexibility and kink resistance properties. The transverse profiles of the strands 662, both as to surface area and as to the ratio of width-to-thickness, can be selected to influence these characteristics. For example, structural strength can be increased by increasing the strand width while maintaining the same thickness. Flexibility can be increased by increasing the pic axial length. Another factor influencing the desired characteristics is the braid angle of the filament strand windings, i.e., the angle of each helical strand 662 with respect to a longitudinal central axis. Increasing the braid angle tends to increase the torqueability while reducing the pushability. In short, strands 662 and arrangements of the strands 662 can be selected to customize the catheter's properties.

In the example of FIG. 6, the braid member 634 includes 16 stainless steel strands 662 having a braid angle of about 45 degrees along the axis of the catheter. Other braid angle ranges from 20 degrees to 60 degrees, for example, are also suitable. The braid member 634 can be stretched axially as it is placed upon the liner 632 during manufacture. When the coil layers 636, 638 and the polymer cover 640 are placed over the braid member 634, the braid member 634 can assume an unbiased configuration. In various examples, strands 662 of the braid member 634 can have a thickness ranging from 0.010 mm to 0.015 mm, but both larger and smaller strand thicknesses can also be used. Widths of the strands 662 can also vary. Some embodiments use strand widths in the range of about 0.057 mm to 0.070 mm.

The multiple coil layers, which can surround the braid member 634, include a first coil layer 636 composed of one or more wires 664 wound in a first direction and a second coil layer 638 composed of one or more wires 666 wound in a second direction, opposing the first direction. The second coil layer 638 can be positioned around and in contact with the first coil layer 636. In use, the wires 664, 666 of the first and second coil layers 636, 638 can interlock and provide the catheter with bi-directional torqueability and pushability capabilities. For example, if one wire 664, 666 in a coil layer has a tendency to kink or bend in use, particularly under influence of a proximally-applied load, the other wires 664, 666 in the same layer or the adjacent layer can support it and inhibit kinking.

The wires 664, 666 can include a fully-rounded cross-section and can vary in size, number, and pitch between the first coil layer 636 and the second coil layer 638 to alter structural properties of the catheter. Wire properties can be selected to balance desired structural properties, such as pushability, torqueability, and flexibility. In an example, each coil layer can include 12 wires having a diameter of about 0.050 mm. Each of the 12 wires can have a uniform pitch that is equal to or greater than about 0.623 mm. Adjacent wires of the 12 wire grouping can be view as having a pitch that is equal to or greater than about 0.072 mm, with a small gap distributed throughout each 12 wire grouping. The size of the pitch can depend on the diameter of the wires, the diameter of the inner lumen 660 and the number of wires in the layer.

The polymer cover 640 can surround the coil layers 636, 638 and, in light of the liner 632, can form the second of two polymer layers included in the shaft body 606. The polymer cover 640 can include a low-friction polymer to reduce the forces required to advance the catheter through vasculature, or a polymer with low viscosity at melting temperatures to allow flow through and around the coil layers 636, 638 and the braid member 634, the latter of which is shown in FIG. 8. In an example, the polymer cover 640 is composed of polyether block amide (commonly referred to as PEBAX, a registered trademark of Arkema France Corporation). The polymer cover 640 can be applied to the coil layers 636, 638 after they are wound into a tubular shape via an extrusion, molding or shrink tubing process, and can be applied thicker along a proximal portion of the shaft body 606 than along a distal portion of the shaft body to enhance distal flexibility and provide a smaller leading diametrical size. In an example, the proximal portion includes an outer diameter 609 (see FIG. 6) between 0.9 mm-1.1 mm and the distal portion includes an outer diameter 909 (see FIG. 9) between 0.8-1.0 mm.

A hydrophilic coating can be provided on the outer surface 656 of the shaft body 606 for lubricious delivery and to aid in steerability. The hydrophilic coating can be thin and constitute only a minor part of the wall thickness of the shaft body 606.

Figure 7:
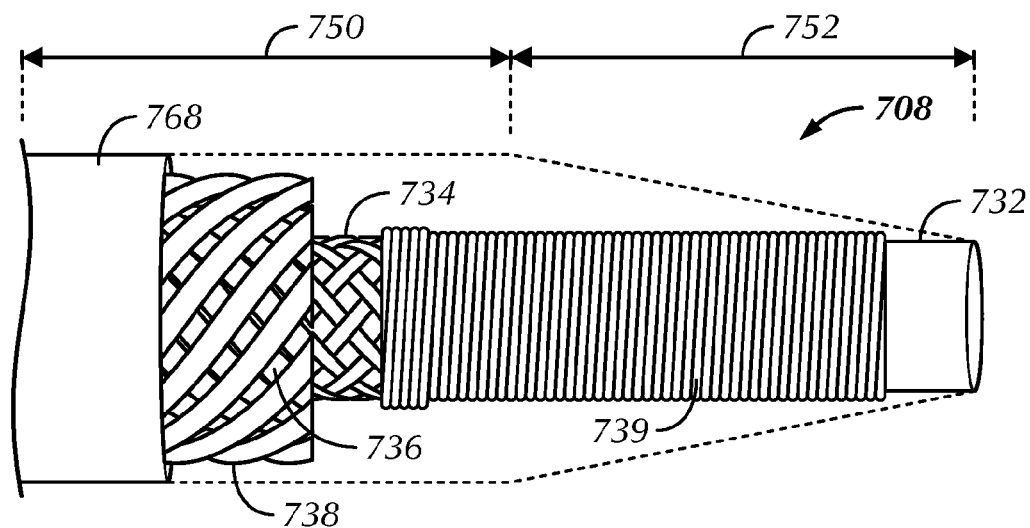
FIG. 7 illustrates a cutaway of a catheter's polymer tip member, as constructed in accordance with at least one embodiment.

FIG. 7 illustrates the multiple components of a catheter's polymer tip member 708, including a liner 732, a distal end of a braid member 734, a distal end of a coil member having multiple coil layers 736, 738, one or more filaments 739, and a polymer cover 768. Staggered stopping points for these components can provide a gradual change in structural properties—pushability, torqueability, flexibility and/or kink resistance—between the tip member 708 and a shaft body and/or between a non-tapered proximal portion 750 of the tip member 708 and a tapered distal portion 752 of the tip member 708. The liner 732 can extend through the proximal 750 and distal 752 portions of the tip member 708, while the braid member 734 and the coil layers 736, 738 can terminate in the proximal portion 750. In the example shown, the braid member 734 extends further into the proximal portion 750 of the tip member 708 than the coil layers 736, 738. The one or more filaments 739 can extend from a position overlapping or underlapping the distal end of the braid member 734 on their proximal ends to a position at or near the distal end of the tip member 708 on their distal ends. In other examples, the one or more filaments 739 can extend from a position overlapping or underlapping the distal end of the coil members 736, 738 on their proximal ends to a position at or near the distal end of the tip member 708 on their distal ends. In still another example, the one or more filaments 739 can be in axial abutment with the distal end of the braid member 734 or the coil members 736, 738.

The one or more filaments 739 can have an appropriate dimension and shape to achieve a desired torqueability, flexibility, and/or other structural characteristic. For example, the filaments 739 can be round, flat, oval, rectangular, square, triangle, polygonal or any other suitable shape. The filaments 739 can be wrapped in a helical manner, with the pitch of adjacent filament turns tightly wrapped, so that each turn touches the succeeding turn, or with the pitch set such that filaments 739 are wrapped in an open fashion. The pitch can be constant throughout the length of the filament 739 windings or can vary, depending upon the desired characteristics for the catheter and specifically the tip member 708. For example, in some embodiments, the filament 739 windings can include a distal portion including a relatively open pitch and a proximal portion having a relatively more closed pitch, such that the windings are more flexible in the distal portion and have a greater ability to transfer toque in the proximal portion.

Clinical bench testing has demonstrated that a tip member 708 including fifteen (15) fiber filaments 739 arranged in a series of contacting helically windings about the braid member 734 on their proximal portions and wound about the liner 732 on their intermediate and distal portions can nearly double the maximum torque load that can be applied before tip failure (e.g., tip shearing). In such example, each filament 739 can have a diameter of about 0.01-0.03 mm. The contacting arrangement of the filaments 739 provides multiple points of failure that must be overcome before the tip member 708 fails. It is believed that more or less filaments 739 (e.g., 2-25 filaments) can be used while still receiving the benefit of increased maximum torque load. Polymer materials such as high density and linear polyolefins and polyesters, fiber materials such as Kevlar® fibers (which are commercially available from DuPont), Vectran® fibers (which are commercially available from Kuraray Co., Ltd.) and carbon fibers, or thin metallic materials can be used to form the filaments 739.

FIGS. 8 and 9 respectively illustrate cross-sections of a proximal portion and a distal portion of a shaft body 806, 906, such as along lines 8-8 and 9-9 of FIG. 3. As shown, a polymer cover 840, 940 can extend inward and seal around first and second coil layers 836, 838, 936, 938 and a braid member 834, 934. Inherent elasticity of the polymer cover 840, 940 can allow wires 864, 866, 964, 966 of the coil layers 836, 838, 936, 938 to make small movements so that the flexibility of the coil layers is maintained; the elasticity also allows the shaft body wall to stay leak-proof when the wires move. The polymer cover 840, 940 can terminate at the distal end of the shaft body 806, 906, proximal to a tip member.

FIGS. 10 and 11 illustrate cross-sections of a non-tapered proximal portion and a tapered distal portion of a polymer tip member 1008, 1108, which is coupled with a distal end of a shaft body. Distal ends of first and second coil layers 1036, 1038, a braid member 1034, and a liner 1032, 1132 can extend into the tip member 1008, 1108. One or more filaments 1139 can extend from a position near the ends of the coil layers 1036, 1038 or the braid member 1034 to a position near the distal end of the tip member 1008, 1108. Each of these components can be surrounded by a polymer that is optionally impregnated with a radiopaque material. The polymer 1068, 1168 of the tip member 1008, 1108 can optionally have a higher viscosity at melting temperatures such that reduced flow through or around the coil layers 1036, 1038, the braid member 1034, or the filaments 1139 occurs during manufacture steps performed at an elevated temperature. In an example, the polymer of the tip member is pellethane and the void space 1070, 1170 existing within the polymer 1068, 1168 can provide the catheter's distal end portion with increased flexibility relative to the shaft body.

Figure 12:
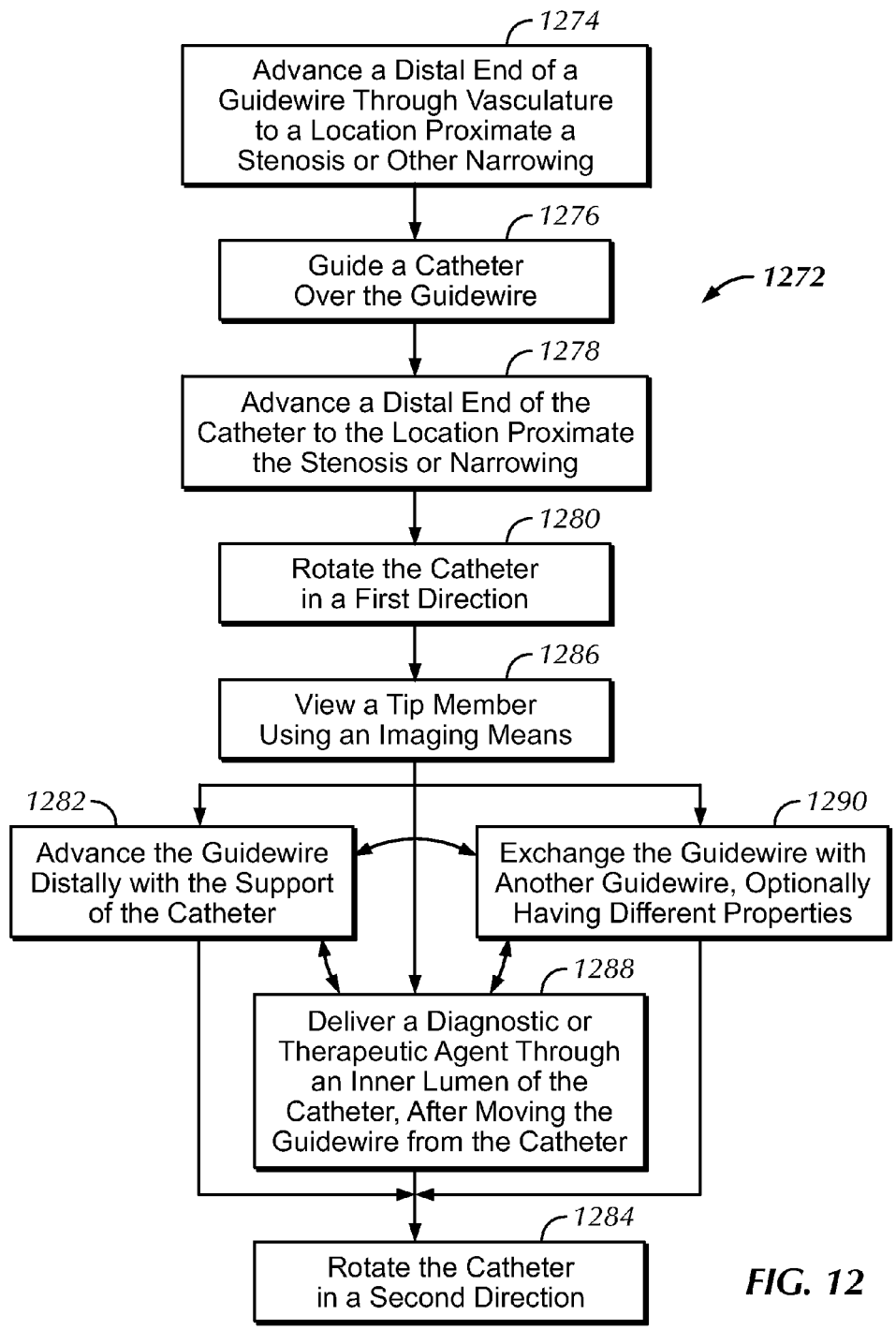
FIG. 12 illustrates a method of using a catheter to navigate through vasculature, as constructed in accordance with at least one embodiment.

FIG. 12 illustrates a method 1272 of using a catheter to navigate through vasculature, as constructed in accordance with at least one embodiment.

At step 1274, the method can include advancing a distal end of a guidewire through vasculature to a location proximate a stenosis or other narrowing in a blood vessel. At step 1276, a catheter can be guided over the guidewire by inserting its proximal end into an inner lumen of the catheter from the catheter's distal end. The inner lumen can be defined, in part, by a liner, a braid member, a coil member, one or more polymer filaments, and a polymer cover. Using the guidewire as a rail, a distal end of the catheter can be advanced to the location proximate the stenosis or narrowing at step 1278.

The catheter can be rotated in a first direction at step 1280, engaging one or more optionally helical threads on an outer surface of the polymer cover with the stenosis or wall of the blood vessel. This engagement between the helical threads and the stenosis or vessel wall can propel the catheter forward in a distal direction. Incremental rotation of the catheter, particularly the catheter's proximal end, can allow incremental movement of the catheter relative to the stenosis or vessel wall.

At step 1282, the guidewire can be advanced distally with the support of the catheter. The method can be configured such that the distal end of the guidewire is at all times distal to the distal end of the catheter.

The catheter can be withdrawn from the blood vessel at step 1284 by rotating its proximal end in a second direction, opposite the first direction. Rotation of the catheter, whether in the first direction or the second direction, can cause wires of the first and second coil layers to engage.

Additional method steps are also possible. At step 1286, the method can optionally include viewing a tip member using an imaging means. At step 1288, the method can optionally include delivering a radiopaque, diagnostic or therapeutic agent through the inner lumen of the catheter. And at step 1290, the method can optionally include exchanging the guidewire advanced to the location proximate the stenosis or narrowing with a second guidewire.

Closing Notes:

The present catheters and related methods include or use a multi-component shaft body and tip member. The multi-component shaft body and tip member can provide catheters with a favorable balance of structural characteristics including pushability, torqueability, flexibility and resistance to kinking. First and second helically-wound coil layers of the shaft body and a plurality of helically-wound polymer filaments of the tip member, for example, can provide the catheter with a thin profile while offering enhanced torqueability to the catheter. A braid member can enable a small shaft body diameter for extending through a tortuous path and reaching small vessels and can further provide kink resistance.

The above Detailed Description includes references to the accompanying drawings, which form a part of the Detailed Description. The Detailed Description should be read with reference to the drawings. The drawings show, by way of illustration, specific embodiments in which the present catheters and methods can be practiced. These embodiments are also referred to herein as "examples."

The above Detailed Description is intended to be illustrative, and not restrictive. For example, the above-described examples (or one or more features or components thereof) can be used in combination with each other. Other embodiments can be used, such as by one of ordinary skill in the art upon reviewing the above Detailed Description. Also, various features or components can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a catheter can comprise an elongate shaft body and a polymer tip member. The elongate shaft body can extend from a proximal end to a distal end and define an inner lumen. The polymer tip member can be disposed at the distal end of the shaft body. The shaft body and the tip member can include a liner, one or both of a braid member or a coil member surrounding the liner, and a polymer cover surrounding the braid member or the coil member. The tip member can further include one or more filaments extending from a position overlapping, underlapping, or abutting a distal end of the braid member or the coil member on their proximal ends to a position distal to the braid member or the coil member on their distal ends.

In Example 2, the catheter of Example 1 can optionally be configured such that the one or more filaments include a plurality of polymer filaments.

In Example 3, the catheter of Example 2 can optionally be configured such that the plurality of polymer filaments includes at least 5 polymer filaments.

In Example 4, the catheter of Example 2 can optionally be configured such that the plurality of polymer filaments includes at least 10 polymer filaments.

In Example 5, the catheter of Example 2 can optionally be configured such that the plurality of polymer filaments includes at least 15 polymer filaments.

In Example 6, the catheter of any one or any combination of Examples 2-5 can optionally be configured such that the plurality of polymer filaments is helically-wound around or helically-wound under the braid member or the coil member on their proximal ends and helically-wound around the liner on their distal ends.

In Example 7, the catheter of Example 6 can optionally be configured such that the polymer filaments are positioned in a contacting, side-by-side arrangement.

In Example 8, the catheter of any one or any combination of Examples 1-7 can optionally be configured such that the coil member includes a multi-layer coil having a first coil layer wound in a first direction and a second coil layer, surrounding the first coil layer, wound in a second direction opposing the first direction.

In Example 9, the catheter of Example 8 can optionally be configured such that the first and second coil layers each include a plurality of helically-wound wires having a fully round cross-section.

In Example 10, the catheter of any one or any combination of Examples 1-9 can optionally be configured such that the shaft body and the tip member include both the braid member and the coil member.

In Example 11, the catheter of Example 10 can optionally be configured such that the braid member extends between the liner and the coil member.

In Example 12, the catheter of any one of Examples 10 or 11 can optionally be configured such that the distal end of each of the braid member and the coil member extend beyond the distal end of the shaft body and into the tip member.

In Example 13, the catheter of Example 12 can optionally be configured such that the tip member includes a non-tapered proximal portion and a tapered distal portion. The liner can extend into the non-tapered proximal portion and the tapered distal portion. The braid member and the coil member can extend into the non-tapered proximal portion but not the tapered distal portion.

In Example 14, the catheter of any one or any combination of Examples 1-13 can optionally be configured such that a portion of the shaft body includes a first polymer cover and the tip member includes a second polymer cover different from the first polymer cover.

In Example 15, the catheter of any one or any combination of Examples 1-14 can optionally be configured such that the polymer cover extends inward through voids between successive windings of the coil or voids of the braid member.

In Example 16, the catheter of any one or any combination of Examples 1-15 can optionally further comprise one or more helical threads extending around an outer surface portion of the polymer cover.

In Example 17, the catheter of Example 16 can optionally be configured such that the one or more helical threads are positioned around a distal end portion of the shaft body.

In Example 18, the catheter of any one of Examples 16 or 17 can optionally be configured such that the one or more helical threads are positioned around the tip member.

In Example 19, the catheter of any one of Examples 16-18 can optionally be configured such that the one or more helical threads include a polymer member wound around the polymer cover.

In Example 20, the catheter of Example 19 can optionally be configured such that the polymer member forming the one or more helical threads has a melting point higher than a melting point of the polymer cover.

In Example 21, the catheter of any one or any combination of Examples 16-18 can optionally be configured such that the one or more helical threads include a depression of the outer surface of the polymer cover.

In Example 22, the catheter of any one or any combination of Examples 1-21 can optionally be configured such that all features, components, or other options are available to use or select from.

Certain terms are used throughout this patent document to refer to particular features or components. As one skilled in the art appreciates, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A catheter, comprising: an elongate shaft body extending from a proximal end to a distal end and defining an inner lumen; and a polymer tip member disposed at the distal end of the shaft body, the shaft body and the tip member including a liner, both a braid member and a coil member surrounding the liner, and a polymer cover surrounding the braid member and the coil member, the tip member further including one or more filaments extending from a position overlapping a distal end of the braid member and abutting a distal end of the coil member on proximal ends of the filaments to a position distal to the braid member and the coil member on distal ends of the filaments.

2. The catheter of claim 1, wherein the one or more filaments include a plurality of polymer filaments.

3. The catheter of claim 2, wherein the plurality of polymer filaments includes at least 5 polymer filaments.

4. The catheter of claim 2, wherein the plurality of polymer filaments includes at least 10 polymer filaments.

5. The catheter of claim 2, wherein the plurality of polymer filaments is helically-wound around the braid member and abutting the coil member on the proximal ends of the filaments and helically-wound around the liner on the distal ends of the filaments.

6. The catheter of claim 5, wherein the polymer filaments are positioned in a contacting, side-by-side arrangement.

7. The catheter of claim 1, wherein the coil member includes a multi-layer coil having a first coil layer wound in a first direction and a second coil layer, surrounding the first coil layer, wound in a second direction opposing the first direction.

8. The catheter of claim 7, wherein the first and second coil layers each include a plurality of helically-wound wires having a fully round cross-section.

9. The catheter of claim 1, wherein the braid member is positioned between the liner and the coil member.

10. The catheter of claim 1, wherein the distal end of each of the braid member and the coil member extend beyond the distal end of the shaft body and into the Up member.

11. The catheter of claim 10, wherein the tip member includes a non-tapered proximal portion and a tapered distal portion, the liner extending into the non-tapered proximal portion and the tapered distal portion, the braid member and the coil member extending into the non-tapered proximal portion but not the tapered distal portion.

12. The catheter of claim 1, wherein a portion of the shaft body includes a first polymer cover and the tip member includes a second polymer cover different from the first polymer cover.

13. The catheter of claim 1, wherein the polymer cover extends inward through voids between successive windings of the coil or voids of the braid member.

14. The catheter of claim 1, further comprising one or more helical threads extending around an outer surface portion of the polymer cover.

15. The catheter of claim 14, wherein the one or more helical threads are positioned around a distal end portion of the shaft body.

16. The catheter of claim 14, wherein the one or more helical threads include a polymer member wound around the polymer cover.

17. The catheter of claim 16, wherein the polymer member forming the one or more helical threads has a melting point higher than a melting point of the polymer cover.

18. The catheter of claim 14, wherein the one or more helical threads include a depression of the outer surface of the polymer cover.

* * * * *

UNITED STATES PATENT AND TRADEMARK OFFICE
CERTIFICATE OF CORRECTION

PATENT NO. : 9,782,561 B2  
APPLICATION NO. : 14/860997  
DATED : October 10, 2017  
INVENTOR(S) : Chad Kugler et al.

Page 1 of 1

It is certified that error appears in the above-identified patent and that said Letters Patent is hereby corrected as shown below:

In the Claims

In Claim 10, Column 12, Line 36, delete "Up" and insert --tip--.

Signed and Sealed this
Twenty-first Day of November, 2017

Joseph Matal
*Performing the Functions and Duties of the
Under Secretary of Commerce for Intellectual Property and
Director of the United States Patent and Trademark Office*